United States Patent
Umebayashi et al.

(10) Patent No.: US 8,273,003 B2
(45) Date of Patent: Sep. 25, 2012

(54) WEB FOLDING APPARATUS, WEB FOLDING METHOD, AND WORN ARTICLE PRODUCING METHOD

(75) Inventors: Toyoshi Umebayashi, Osaka (JP); Takahiro Shimada, Osaka (JP)

(73) Assignee: Zuiko Corporation, Osaka (JP)

( * ) Notice: Subject to any disclaimer, the term of this patent is extended or adjusted under 35 U.S.C. 154(b) by 562 days.

(21) Appl. No.: 12/600,844

(22) PCT Filed: Apr. 24, 2008

(86) PCT No.: PCT/JP2008/057907
§ 371 (c)(1),
(2), (4) Date: Nov. 19, 2009

(87) PCT Pub. No.: WO2008/142946
PCT Pub. Date: Nov. 27, 2008

(65) Prior Publication Data
US 2010/0168708 A1 Jul. 1, 2010

(30) Foreign Application Priority Data
May 24, 2007 (JP) .................................. 2007-137537

(51) Int. Cl.
*B31F 1/08* (2006.01)
(52) U.S. Cl. ........ 493/417; 493/402; 493/416; 493/422; 493/424; 493/454
(58) Field of Classification Search .................. 493/402, 493/405, 416, 417, 422, 423–424, 441, 454
See application file for complete search history.

(56) References Cited

U.S. PATENT DOCUMENTS 4,784,379 A * 11/1988 Vander Syde et al. ..... 270/58.06
5,035,683 A * 7/1991 Takeda et al. ................... 493/23
(Continued)

FOREIGN PATENT DOCUMENTS

JP 58-87748 6/1983
(Continued)

OTHER PUBLICATIONS

International Search Report for corresponding Application No. PCT/JP2008/057907 dated May 12, 2008.

*Primary Examiner* — Christopher Harmon
(74) *Attorney, Agent, or Firm* — Renner, Otto, Boisselle & Sklar, LLP

(57) ABSTRACT

An apparatus of the present invention includes: a folding section 2 for folding a web W in two so that opposite side edges Wa and Wb of the web W are brought into a predetermined positional relationship with each other by bringing the web W into contact with an abutting member 4; a pair of carrying means 10A and 10B arranged along opposite sides of the web W for carrying the web W in the longitudinal direction X; a plurality of holding means 20 provided in each of the carrying means 10A and 10B wherein the holding means 20 can be displaced in the transverse direction D of the web W; displacement means 30 for displacing the holding means 20 in the transverse direction D upstream of the abutting member 4 so as to correct a positional relationship between the web W and the abutting member 4; detection means 3 for outputting positional information regarding a position of the web W in the transverse direction D; and control means 200 for controlling the displacement means 30 based on the positional information.

5 Claims, 5 Drawing Sheets

U.S. PATENT DOCUMENTS

| | | | |
|---|---|---|---|
| 5,520,604 A * | 5/1996 | Reist | 493/422 |
| 5,902,222 A * | 5/1999 | Wessman | 493/439 |
| 5,997,459 A * | 12/1999 | Kruger et al. | 493/441 |
| 6,565,501 B1 * | 5/2003 | Trennepohl | 493/423 |
| 6,913,664 B2 | 7/2005 | Umebayashi et al. | |
| 7,500,941 B2 * | 3/2009 | Coe et al. | 493/438 |
| 2005/0026760 A1 | 2/2005 | Yamamoto et al. | |

FOREIGN PATENT DOCUMENTS

| | | |
|---|---|---|
| JP | 5-95915 | 12/1993 |
| JP | 6-1322 | 1/1994 |
| JP | 2003-038566 | 2/2003 |
| JP | 2005-046246 | 2/2005 |

* cited by examiner

WEB FOLDING APPARATUS, WEB FOLDING METHOD, AND WORN ARTICLE PRODUCING METHOD

TECHNICAL FIELD

The present invention relates to a web folding apparatus, a web folding method, and a worn article producing method.

BACKGROUND ART

During the process of producing a disposable worn article, a semi-finished product thereof, e.g., a web, is sometimes folded in two. For such a case, methods have been employed, in which the web is brought into contact with a sailor (abutting member) so that the web is folded in two along the sailor.

In order to improve the appearance of a package or a product, it is important to bring the edges of the opposite sides of the web into a predetermined positional relationship, e.g., a state where the opposite side edges are aligned with each other. In some cases, a predetermined function of a worn article is implemented by achieving such a predetermined positional relationship.

In view of this, methods have been proposed in the art for correcting the web-carrying path based on the positional information of the opposite side edges of the web so that the opposite side edges of the web are brought into a predetermined positional relationship (see the first patent document).

[First Patent Document] Japanese Laid-Open Patent Publication No. 2003-38566 (Abstract)

The first patent document describes a method including placing an elastic member on the surface of a web, layering an absorbent body thereon, forming holes to be leg holes in the web, and then folding the web in two by a sailor so that the opposite side edges are brought into a predetermined positional relationship.

DISCLOSURE OF THE INVENTION

Even with the production method of the first patent document, however, there is sometimes a misalignment between the edges of the opposite sides of a folded web.

In view of this, the present inventors made researches on the causes of the misalignment to find out that the misalignment occurs due to reasons as follows.

(1) Even if the web-carrying path is corrected by using a web guider, or the like, before the web is folded, the web may move in either way in the transverse direction, which is generally perpendicular to the carrying direction, when the web contacts the sailor, thus resulting in the misalignment.

(2) The member forming the web is not uniform materialwise, and may vary in elasticity from one area to another. Moreover, the thickness of the web may also vary, with another sheet, an absorbent body, etc., layered thereon. Therefore, even if the web-carrying path is corrected, the web may move in either way in the transverse direction during the process of contacting the web with the sailor and thereby folding the web, thus resulting in such a misalignment as described above, due to the variations in the elasticity or the thickness of the web.

(3) Since it is difficult to precisely machine the sailor itself into a shape that is symmetrical in the left-right direction, there may occur such a misalignment as described above during the process of folding in two, due to the shape of the sailor.

It is therefore a primary object of the present invention to provide a web folding apparatus, a web folding method and a worn article producing method, with which when a web is folded in two, the opposite side edges of the web can be brought into a predetermined positional relationship with each other.

In order to achieve the object set forth above, a web folding apparatus of the present invention includes: a folding section for folding a continuous web in two so that opposite side edges of the web in a transverse direction between which an intermediate portion of the web is in are brought into a predetermined positional relationship with each other by bringing the intermediate portion of the web into contact with (by pressing the intermediate portion of the web against) an abutting member extending in a longitudinal direction of the web; a pair of carrying means arranged along opposite sides of the web being folded in the folding section for carrying the web in the longitudinal direction; a plurality of holding means provided in each of the carrying means for moving in the longitudinal direction together with the web while holding side portions of the web along the longitudinal direction at least up to an upstream end portion of the abutting member wherein the holding means can be displaced in the transverse direction of the web; displacement means for displacing the holding means in the transverse direction in, or upstream of, the upstream end portion of the abutting member so as to correct a positional relationship between the web to be in contact with the abutting member and the abutting member; detection means for detecting a reference (detected) portion in the web serving as a reference for two-fold folding to thereby output positional information regarding a position of the web in the transverse direction; and control means for controlling the displacement means based on the positional information.

According to the present invention, the holding means are moved, by an amount corresponding to the displacement of the web in the transverse direction, while holding the side portions at least up to the upstream end portion of the abutting member. Therefore, it is possible to bring the web into contact with the abutting member without misalignment in the transverse direction.

Moreover, in a case where the opposing holding means hold the opposite side portions of the web up to the downstream end portion of the abutting member, it is possible to precisely fold the web so that the opposite side edges of the web are brought into a predetermined positional relationship by constantly maintaining the positional relationship between the abutting member and the web, even if the abutting member itself is not precisely machined into a shape that is symmetrical in the left-right direction.

Note that "the intermediate portion of the web in the transverse direction" as used herein refers to a portion of the web excluding opposite side portions thereof in the transverse direction. The side portion of the web refers to a side edge (edge) parallel to the longitudinal direction (flow direction) of the web, and the vicinity thereof.

The term "abutting member" not only is a member to be in contact with the web which is pressed thereagainst, but also is a folding member for folding the web in contact therewith into a V-letter shape.

While a web is typically folded in two so that opposite side edges thereof are aligned with each other in the present invention, it is not always necessary that the opposite side edges are aligned with each other. That is, it is only necessary in the present invention that a web is folded in two so that the opposite side edges are in a predetermined positional relationship. For example, a web may be folded in two so that one side edge sticks out from the other side edge by a predetermined amount.

Typically, as the "reference (detected) portions", opposite side edges of a web are detected. However, in a case where a graphical pattern or a picture is printed on the web, or where the web has holes, depressions and protrusions thereon, they may alternatively be detected as the reference portions, and subjected to an image processing operation, based on which positional information of the web is produced.

The detecting section for detecting the reference portion may be an ultrasonic sensor, an optical sensor (e.g., an infrared sensor), an air sensor, etc. Alternatively, the deviation of the web may be detected by processing an image obtained by using a CCD camera or a one-dimensional linear sensor (line sensor).

The type of a sensor is appropriately selected depending on the type of the web. For example, in a case where the air can be easily passed through the web, it is preferred to use an ultrasonic sensor or an optical sensor. In a case where the web is transparent or semitransparent, it is preferred to use an ultrasonic sensor or an air sensor.

In a preferred example of the present invention, the carrying means are arranged so that the holding means provided in one carrying means and the holding means provided in the other carrying means come closer to each other as the holding means move downstream in a carrying direction of the web. Thus, as the opposing holding means come closer to each other, it is possible to precisely fold the web in two while keeping the web in contact with the abutting member.

In a preferred example of the present invention, the holding means is moved around in a loop by the carrying means, and the holding means holds the web in an area from which the holding means moves downstream together with the web, and releases the hold of the web before reaching an area from which the holding means moves in an opposite direction to a flow of the web. In such a case, since the hold of the web is released before the holding means moves in the opposite direction to the flow of the web, no undue force acts upon the web.

In order to achieve the object set forth above, a web folding method of the present invention is a web folding method for folding a continuous web in two along a line extending in a longitudinal direction of the web, the method including the steps of: carrying the web; detecting a reference (detected) portion in the web serving as a reference for two-fold folding to thereby produce positional information regarding a position of the reference portion; holding opposite side portions of the web along the longitudinal direction by holding means, wherein the holding means can move in the longitudinal direction of the web while holding the web, and can be displaced in a transverse direction of the web; correcting a path of the web by displacing a position of the holding means in the transverse direction based on the positional information so that opposite side edges of the web when folded in two come closer to a predetermined positional relationship; and folding the web in two so that the opposite side edges of the web being held are brought into the predetermined positional relationship.

A worn article producing method using the web folding method further includes, before the step of folding the web in two, the steps of: arranging an elastic member on a surface of the web; layering an absorbent body on the surface of the web; and forming a hole to be a leg hole in the web.

Note that the term "worn article" as used herein is a concept encompassing semi-finished and finished products of disposable worn articles such as disposable diapers and disposable pants.

DESCRIPTION OF THE REFERENCE NUMERALS

Figure 1:
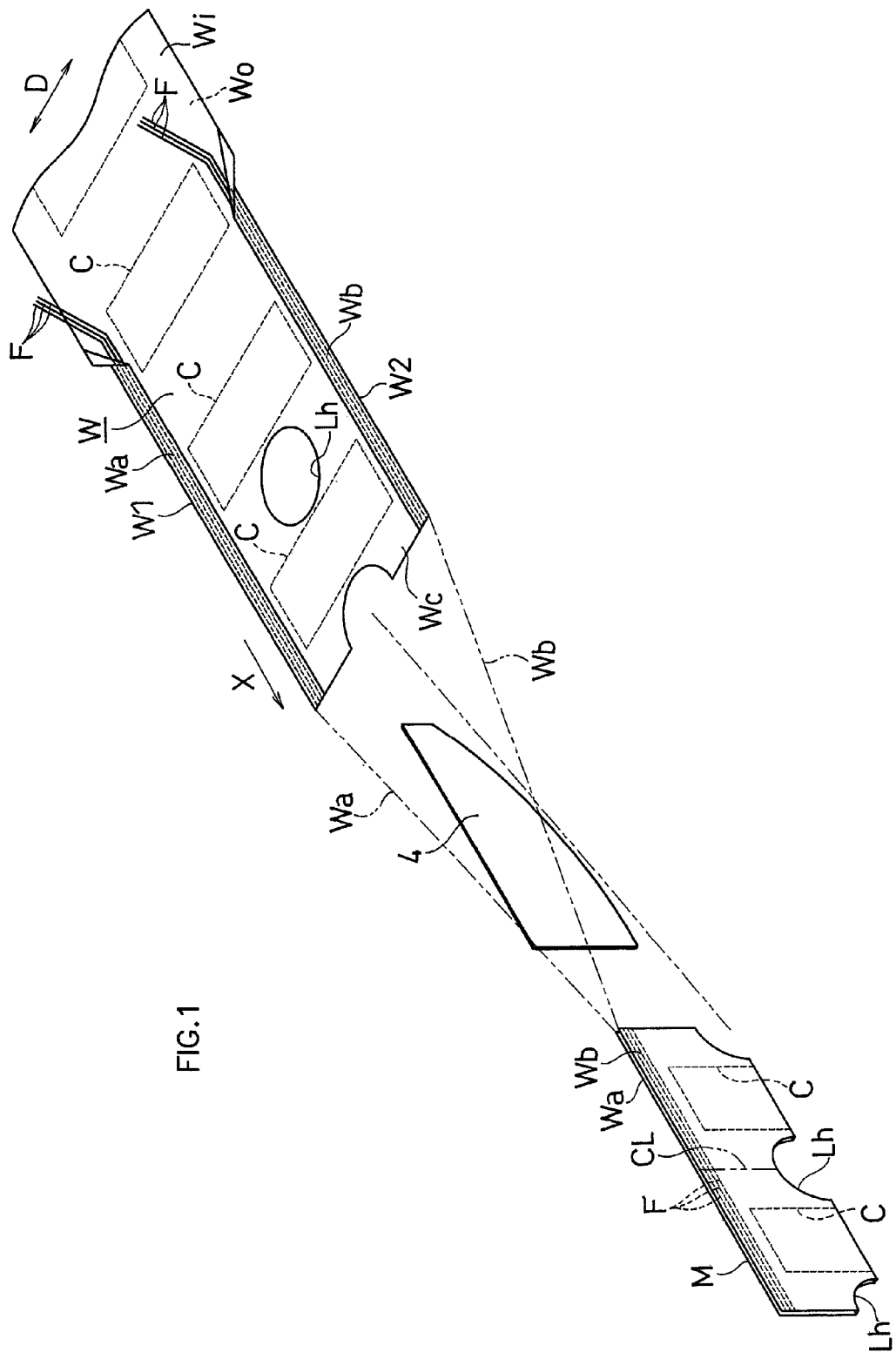
FIG. 1 is a schematic perspective view showing a web folding method according to Embodiment 1 of the present invention.

1: Folding apparatus
10A, 10B: Carrying means
2: Folding section
20: Holding means
200: Control means
3: Detection means
30: Displacement means
C: Absorbent body
D: Transverse direction
F: Elastic member
Lh: Leg hole
W: Web
W1, W2: Side edge (reference portion)
Wa, Wb: Side portion
Wc: Intermediate portion
X: Longitudinal direction

BEST MODE FOR CARRYING OUT THE INVENTION

The present invention will be understood more clearly from the following description of a preferred embodiment taken in conjunction with the accompanying drawings. Note however that the embodiment and the drawings are merely illustrative and should not be taken to define the scope of the present invention. The scope of the present invention shall be defined only by the appended claims. In the accompanying drawings, like reference numerals denote like components throughout the plurality of figures.

Embodiment 1

One embodiment of the present invention will now be described with reference to the drawings.

Note that the following description is directed to an illustrative case where a web W is folded in two along the center of the web W in the transverse direction D so that opposite side edges W1 and W2 of the web W are aligned with each other, as shown in FIG. 1.

As shown in FIG. 1, the web W includes a continuous outer sheet Wo and a continuous inner sheet Wi, with an absorbent body C arranged between the two sheets Wo and Wi. The web W is also provided with elastic members F formed by rubber threads, for example, arranged along opposite side portions Wa and Wb of the web W, and holes Lh to be leg holes perforated in an intermediate portion Wc of the web W in the transverse direction D.

The web W is carried to a web folding apparatus 1 (FIG. 2), where the intermediate portion Wc thereof is folded in two by the folding apparatus 1 so that the opposite side edges W1 and W2 are aligned with each other, and then the web W is cut along the cut-off line CL into individual diapers M (an example of a worn article).

Figure 2:
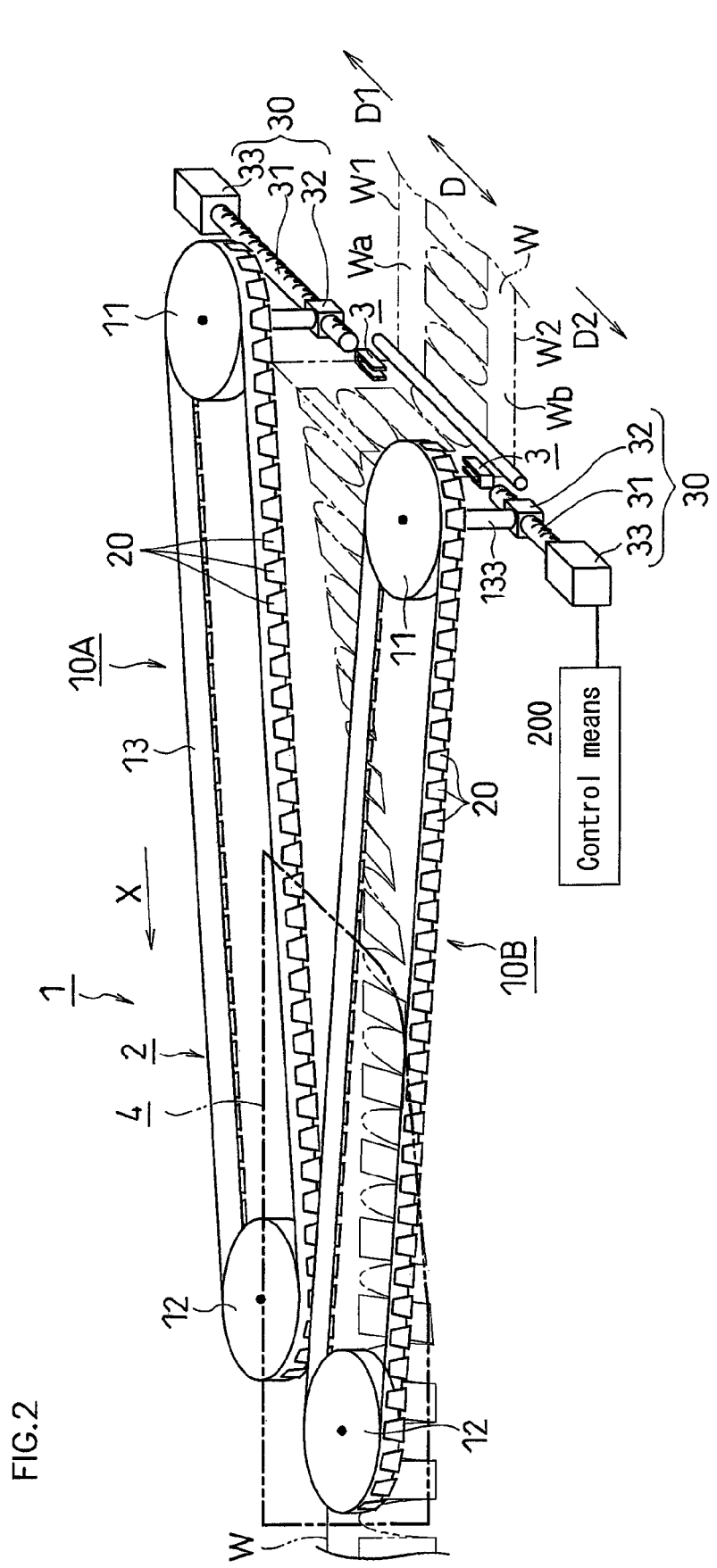
FIG. 2 is a schematic perspective view showing a folding apparatus.

Folding Apparatus 1:

As shown in FIG. 2, the folding apparatus 1 includes a folding section 2 for folding the web W in two, and a pair of carrying means 10A and 10B arranged along the opposite sides of the web W, which is folded in the folding section 2, for carrying the web W in the longitudinal direction (flow direction) X.

Each carrying means 10A, 10B includes a downstream driver pulley 12 to be spun by a driver unit (not shown) and an upstream follower pulley 11, with an endless belt 13 wound around the follower pulley 11 and the driver pulley 12. The belt 13 includes many holding means 20 to be described below.

Figure 4:
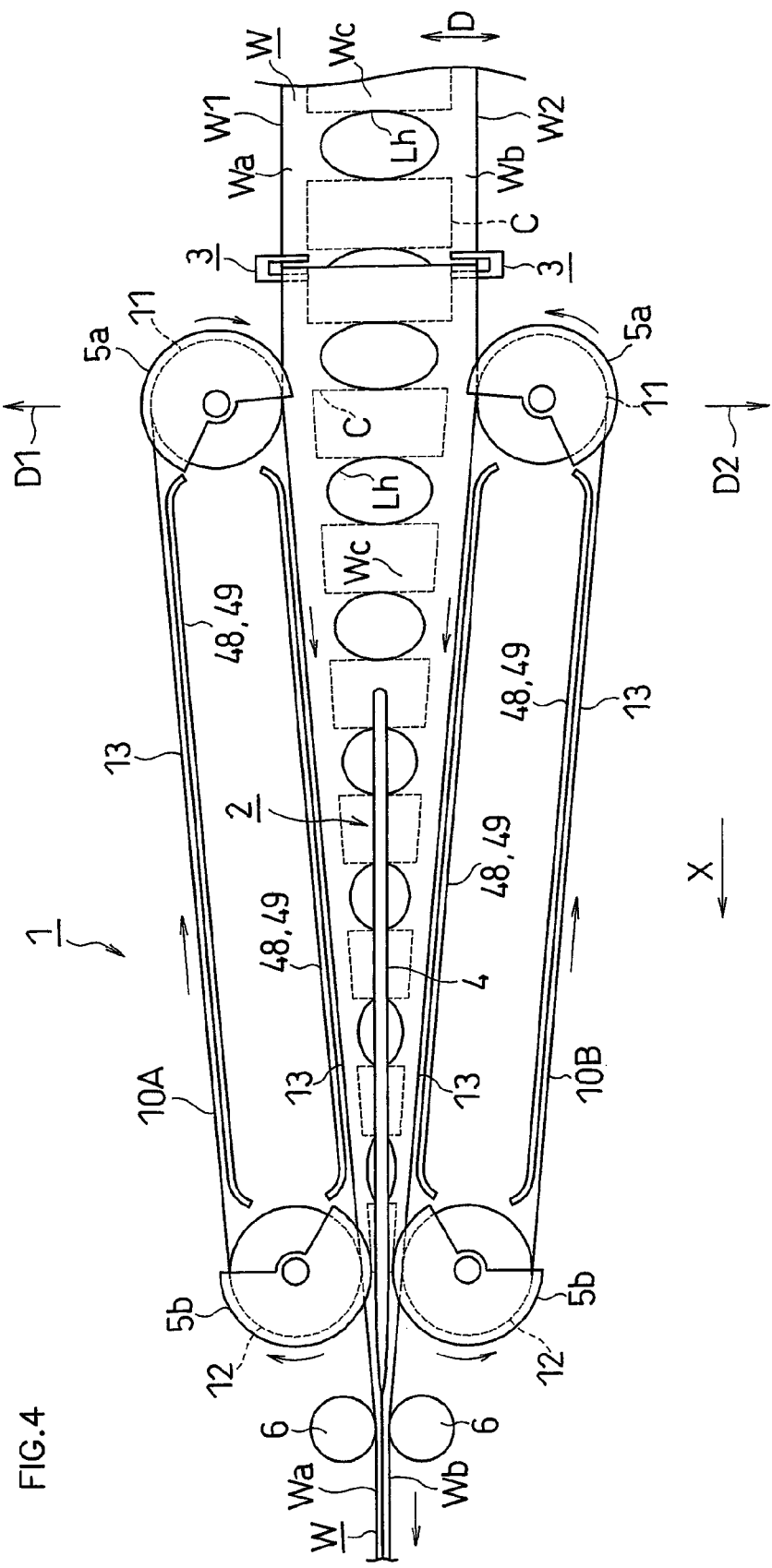
FIG. 4 is a schematic plan view showing the folding apparatus.

As shown in FIG. 4, the upstream pair of follower pulleys 11 are provided spaced apart from each other so as to stand close to the side portions Wa and Wb of the unfolded web W, and the downstream pair of driver pulleys 12 are arranged close to each other. Therefore, as shown in FIGS. 2 and 4, the belts 13 wound around the follower pulleys 11 and the driver pulleys 12 are arranged in a generally V-shaped pattern as viewed from above so that the holding means 20 provided in one carrying means 10A (10B) of FIG. 2 and the holding means 20 provided in the other carrying means 10B (10A) come closer to each other as they move downstream in the carrying direction X of the web W.

In the folding section 2, an abutting member (sailor) 4 extending in the longitudinal direction X of the continuous web W is provided between the opposite carrying means 10A and 10B. As the web W is carried along while being held by the holding means 20, the intermediate portion Wc of the web W is brought into contact with the lower end of the abutting member 4, thereby folding the web W in two so that the opposite side portions Wa and Wb are laid on each other.

Figure 3:
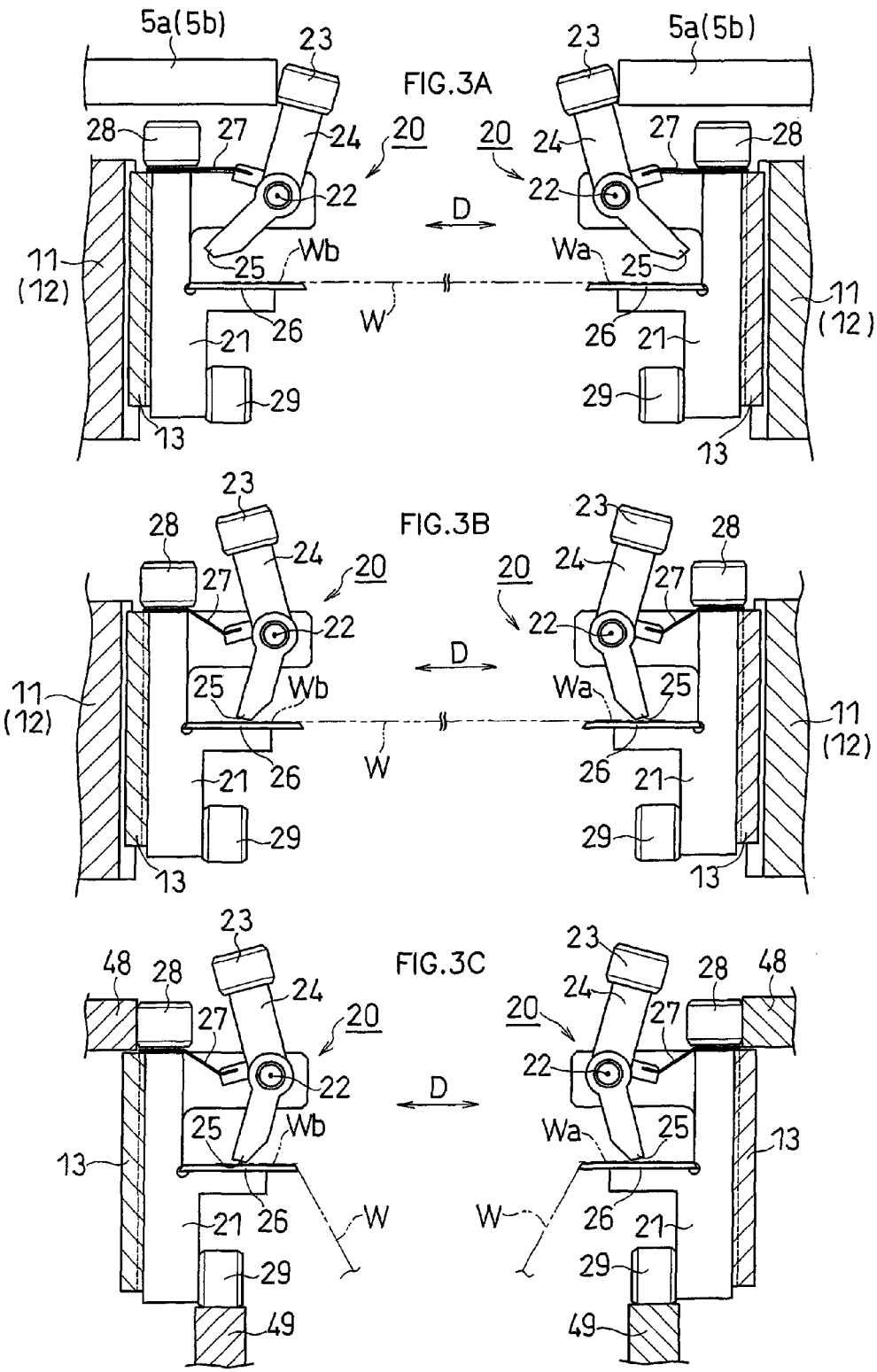
FIGS. 3A, 3B and 3C are schematic cross-sectional views each showing holding means.

Holding Means 20:

As shown in FIG. 3B, the holding means 20 includes a holding means main body 21, and a pivoting section 24 pivotally attached to the holding means main body 21 about a pivot center 22.

The holding means main body 21 is fixed to the belt 13. A clamping table 26 is fixed to the holding means main body 21. The side portion Wa, Wb of the web W is introduced onto the upper surface of the clamping table 26.

A leaf spring 27 is attached to the pivoting section 24, with one end portion of the leaf spring 27 fixed to the holding means main body 21. A lower end 25 of the pivoting section 24 is urged into a closed state in which it is pressed against the clamping table 26 by the spring force of the leaf spring 27.

As shown in FIG. 3A and FIG. 4, a cam (opener) 5a (5b) is fixed above the pulley 11 (12). As shown in FIG. 3A, a runner 23, to be in contact with the cam 5a (5b), is provided at the upper end of the pivoting section 24. As the runner 23 contacts the cam 5a (5b), the pivoting section 24 pivots about the pivot center 22, and the lower end 25 of the pivoting section 24 comes off the clamping table 26, thus transitioning the holding means 20 from the closed state (hold state) to the open state (release state).

As shown in FIG. 4, first and second guide rails 48 and 49 are provided between the follower pulley 11 and the driver pulley 12. As shown in FIG. 3C, first and second rollers 28 and 29 are attached to the holding means main body 21. With the first and second rollers 28 and 29 guided along the first and second guide rails 48 and 49, the attitude of the holding means main body 21 is maintained between the follower pulley 11 and the driver pulley 12.

As shown in FIG. 2, the holding means 20 is moved around in a loop by the carrying means 10A (10B), and the holding means 20 holds the side portion Wa (Wb) of the web W in an area from which it moves downstream together with the web W, and releases the hold of the side portion Wa (Wb) of the web W before reaching an area from which it moves in the opposite direction to the flow direction X of the web W.

That is, as the holding means 20 shown in FIG. 3B reaches the follower pulley 11 of FIG. 4, the pivoting section 24 pivots about the pivot center 22 with the runner 23 thereof contacting the upstream cam 5a, thus bringing the holding means 20 into the open state, as shown in FIG. 3A.

The web W carried from upstream as shown in FIG. 4 is carried onto the clamping table 26 of the holding means main body 21, as shown in FIG. 3A.

As shown in FIG. 3B, as the contact between the runner 23 and the cam 5a is released, the pivoting section 24 pivots about the pivot center 22 toward the clamping table 26 into the closed state by the spring force of the leaf spring 27. Thus, the opposite side portions Wa and Wb of the web W are each clamped between the lower end 25 of the pivoting section 24 and the clamping table 26, thereby holding the side portion Wa, Wb of the web W by means of the holding means 20.

As shown in FIG. 3C, the first and second rollers 28 and 29 are guided along the first and second guide rails 48 and 49, thereby carrying the web W downstream, with the holding means 20 holding the web W.

As the web W is carried in the longitudinal direction X to reach the folding section 2, the intermediate portion Wc (FIG. 1) is folded by the abutting member 4 so that the opposite side portions Wa and Wb of the web W come closer to each other.

As the holding means 20 reaches the driver pulley 12, the pivoting section 24 pivots about the pivot center 22 with the runner 23 of the pivoting section 24 of FIG. 3B contacting the downstream cam 5b, as shown in FIG. 3A, thereby bringing the holding means 20 into the open state and releasing the hold of the side portion Wa, Wb.

Note that the end portion of the lower end 25 preferably has a smooth shape so as to prevent the web W from getting caught on the lower end 25 of the pivoting section 24.

The holding means 20 may be any means as long as it is capable of holding the side portion Wa, Wb of the web W, and may be, for example, means that holds the side portion Wa, Wb of the web W using a vacuum, a needle, a frictional force, etc.

The folding apparatus 1 of FIG. 2 includes detection means 3, displacement means 30 and control means 200 for correcting the positional relationship between the web W to be in contact with the abutting member 4 and the abutting member 4.

Displacement Means 30:

As shown in FIG. 2, the opposite follower pulleys 11 are each provided rotatably about a post 133, which is attached to a slider 32. The slider 32 is formed with a female screw (not shown), which meshes with a male screw 31 extending in the transverse direction D. The male screw 31, the slider 32 and a motor 33 together form the displacement means 30, wherein as the male screw 31 is rotated by the motor 33, the follower pulley 11 is moved in the transverse direction D together with the slider 32.

Detection Means 3:

Upstream of the follower pulley 11, the detection means 3 is provided for detecting the side edge (reference portion) W1, W2 of the web W. The detection means 3 is an optical sensor, for example, and outputs, to the control means 200 of FIG. 2, positional information regarding the position of the side edge W1, W2 in the transverse direction D.

Control Means 200:

Based on the positional information from the detection means 3, the control means 200 controls the motor 33 of the displacement means 30 so as to move the position of the follower pulley 11 together with the slider 32.

That is, if the control means 200 determines that the web W is displaced in the first direction D1 along the transverse direction D with respect to the abutting member 4 (or the center line), based on the positional information of the detection means 3, the control means 200 drives the motor 33 so as to move the slider 32, by an amount corresponding to the amount of displacement, toward the second direction D2, opposite to the first direction D1.

If the control means 200 determines that the web W is displaced in the second direction D2 along the transverse direction D with respect to the abutting member 4 (or the center line), based on the positional information of the detection means 3, the control means 200 drives the motor 33 so as to move the slider 32 in the first direction D1 by an amount corresponding to the amount of displacement.

Here, since the width of the web W in the transverse direction D is generally constant, the opposite follower pulleys 11 are displaced in the same displacement direction D1 (D2) by an amount corresponding to the amount of displacement of the web W in the transverse direction D. However, if the material of the web W is elastic, they may be displaced in different displacement directions D1 (D2).

Since the positions (the positions of the centers) of the opposite driver pulleys 12 are fixed, the intermediate portion Wc of the web W being held by the holding means 20 contacts the abutting member 4 at a constant position, thus enabling precise folding of the web W such that the opposite side edges W1 and W2 of the web W are aligned with each other.

The holding position at which the side portion Wa, Wb is clamped between the lower end 25 of the pivoting section 24 and the clamping table 26 of FIG. 3C is preferably about 5 mm to 10 mm from the side portion of the web W. With the holding position being less than 5 mm, it is difficult to maintain the hold state, and with the holding position being more than 10 mm, the side portion Wa, Wb is likely to get caught on the lower end 25, which may result in a damage to the web W, as the lower end 25 is transitioned to the open state.

Method for Producing Diaper M:

As shown in FIG. 1, after the outer sheet Wo, the absorbent body C and the inner sheet Wi are layered together, the elastic members F formed by rubber threads, for example, are arranged along each side portion Wa, Wb of the web W, and the holes Lh to be leg holes are perforated in the intermediate portion Wc of the web W in the transverse direction D, thus forming the continuous web W.

As the holding means 20 fixed to the belt 13 of FIG. 2 reaches the cam 5a above the follower pulley 11 shown in FIG. 4, the cam 5a and the runner 23 of the pivoting section 24 come into contact with each other, thereby bringing the pivoting section 24 into the open state, as shown in FIG. 3A.

In the open state, the side portion Wa, Wb of the web W is carried onto the clamping table 26 of the holding means 20, and then the holding means 20 moves downstream. Then, as the engagement between the cam 5a (FIG. 4) and the runner 23 is released, the pivoting section 24 is pressed against the clamping table 26 by the spring force of the leaf spring 27, as shown in FIG. 3B, thus entering the hold state (closed state) in which the side portion Wa, Wb is clamped between the lower end 25 of the pivoting section 24 and the clamping table 26.

The holding means 20 attached to the belt 13 shown in FIG. 4 is moved in the longitudinal direction X toward the driver pulley 12 while holding the side portion Wa, Wb of the web W. As the web W reaches the abutting member 4 of the folding section 2, the web W is folded by the abutting member 4 in the intermediate portion Wc of the web W.

As the web W is carried along, the detection means 3 and 3 shown in FIG. 2 respectively detect the opposite side edges W1 and W2 of the web W, which are reference (detected) portions of the web W serving as the reference for the two-fold folding, and produce positional information regarding the positions of the opposite side edges W1 and W2, which are transmitted to the control means 200.

Based on the positional information of the opposite side edges W1 and W2 of the web W from the detection means 3, the control means 200 moves the sliders 32 by controlling the motors 33 of the displacement means 30 to thereby displace the positions of the upstream follower pulleys 11 in the transverse direction D. In this operation, the downstream driver pulleys 12 are not moved.

Therefore, even if the web W is supplied into the folding apparatus 1 while being misaligned in the transverse direction D, the path of the web W is corrected, whereby the abutting member 4 is always contacted by a predetermined portion of the intermediate portion Wc of the web W, i.e., generally the center portion of the web W in the transverse direction D in the illustrated embodiment.

Therefore, even if the web W is displaced in the transverse direction D, the web W can be folded in two at the center of the web W in the transverse direction D so that predetermined portions of the web W, e.g., the side edges W1 and W2, are aligned with each other when they are folded.

Then, as the holding means 20 reaches the cam 5b located above the driver pulley 12 shown in FIG. 4, the runner 23 of the pivoting section 24 of FIG. 3B contacts the downstream cam 5b as shown in FIG. 3A. As a result, the pivoting section 24 pivots about the pivot center 22, and the pivoting section 24 is brought into the open state, thereby releasing the hold of the side portion Wa, Wb. Then, the holding means 20 is moved from the driver pulley 12 toward the follower pulley 11.

After the release, the web W is folded up in two by passing through between a pair of nip rolls 6 and 6 shown in FIG. 4. Then, the web W is carried downstream, and is cut along the cut-off line CL into individual diapers M, as shown in FIG. 1.

Note that in order to precisely maintain a constant positional relationship between the holding means 20 and the opposite side edges W1 and W2 of the web W of FIG. 3A, the holding means 20 may be aligned at a predetermined position by the displacement means 30 before holding the opposite side portions Wa and Wb.

Figure 5:
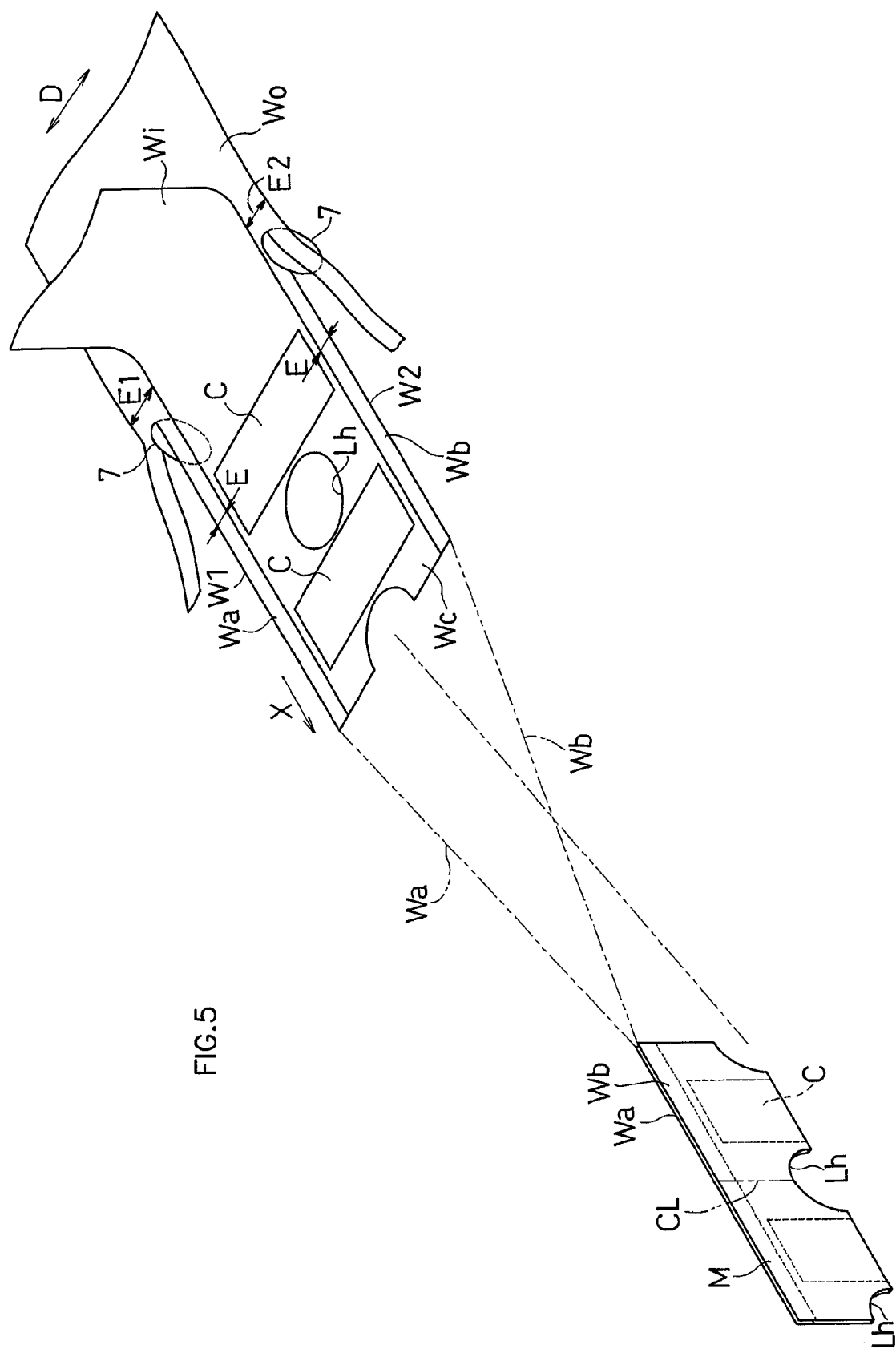
FIG. 5 is a schematic perspective view showing a web folding method according to a variation.

Before the side portion Wa, Wb of the web W is held by the holding means 20, the opposite side portions of the outer sheet Wo of the web W may be cut off by a slitting operation by means of cutters 7 and 7, as shown in FIG. 5. By this process, the intervals (E1 and E2) between the opposite side edges of the outer sheet Wo and those of the inner sheet Wi become an equal value E. As a result, by folding so that the opposite side edges W1 and W2 of the web W are aligned with each other, the opposite side edges of the inner sheet Wi are also aligned with each other.

As shown in FIG. 5, the absorbent body C may be arranged on the inner sheet Wi after the outer sheet Wo and the inner sheet Wi are attached together, and an elastic member may be arranged around the leg hole Lh.

While the above description is directed to a case where the cam 5a, 5b is used to achieve a state transition of the holding means 20 between the open state and the closed state, the transition between the open state and the closed state may be done by means of a magnetic force, an actuator, etc.

While the above description is directed to a case where the web W is folded at the center of the web W in the transverse direction D so that the opposite side edges W1 and W2 of the web W are aligned with each other, the positions of the driver pulleys 12 with respect to the abutting member 4 may be adjusted, whereby the web W is folded in two so that any two intended points on the intermediate portion Wc of the web W are aligned with each other.

INDUSTRIAL APPLICABILITY

The web folding apparatus and the web folding method of the present invention are applicable, for example, to the production of a worn article, or the like, in which a continuous web is used.

The invention claimed is:

1. A web folding apparatus comprising:
a folding section for folding a continuous web in two so that opposite side edges of the web in a transverse direction between which an intermediate portion of the web is in are brought into a predetermined positional relationship with each other by bringing the intermediate portion of the web into contact with an abutting member extending in a longitudinal direction of the web;
a pair of carrying means arranged along opposite sides of the web being folded in the folding section for carrying the web in the longitudinal direction;
a plurality of holding means provided in each of the carrying means for moving in the longitudinal direction together with the web while holding side portions of the web along the longitudinal direction at least up to an upstream end portion of the abutting member wherein the holding means are displaceable in the transverse direction of the web;
displacement means for displacing the holding means in the transverse direction in, or upstream of, the upstream end portion of the abutting member so as to correct a positional relationship between the web to be in contact with the abutting member and the abutting member;
detection means for detecting a detected portion in the web serving as a reference for two-fold folding to thereby output positional information regarding a position of the web in the transverse direction; and
control means for controlling the displacement means based on the positional information.

2. A web folding apparatus according to claim 1, wherein the carrying means are arranged so that one of the holding means provided in one of the carrying means and the other holding means provided in the other carrying means come closer to each other as the holding means move downstream in a carrying direction of the web.

3. A web folding apparatus according to claim 2, wherein the holding means are moved around in a loop by the carrying means, and the holding means hold the web in an area from which the holding means move downstream together with the web, and release the hold of the web before reaching an area from which the holding means move in an opposite direction to a flow of the web.

4. A web folding method for folding a continuous web in two along a line extending in a longitudinal direction of the web, the method comprising the steps of:
carrying the web;
detecting a detected portion in the web serving as a reference for two-fold folding to thereby produce positional information regarding a position of the detected portion;
holding opposite side portions of the web along the longitudinal direction by holding means, wherein the holding means are movable in the longitudinal direction of the web while holding the web, and are displaceable in a transverse direction of the web;
correcting a path of the web by displacing a position of the holding means in the transverse direction based on the positional information so that opposite side edges of the web when folded in two come closer to a predetermined positional relationship; and
folding the web in two so that the opposite side edges of the web being held are brought into the predetermined positional relationship.

5. A worn article producing method, comprising a folding method according to claim 4, the worn article producing method further comprising, before the step of folding the web in two, the steps of:
arranging an elastic member on a surface of the web;
layering an absorbent body on the surface of the web; and
forming a hole to be a leg hole in the web.

* * * * *